(12) United States Patent
Brickell et al.

(10) Patent No.: US 7,457,950 B1
(45) Date of Patent: Nov. 25, 2008

(54) MANAGED AUTHENTICATION SERVICE

(75) Inventors: Erine F. Brickell, Portland, OR (US); Wesley Deklotz, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 595 days.

(21) Appl. No.: 09/676,319

(22) Filed: Sep. 29, 2000

(51) Int. Cl.
*H04L 9/32* (2006.01)
*G06Q 10/00* (2006.01)

(52) U.S. Cl. .............................. 713/156; 705/1; 705/2; 705/3; 705/51; 705/56

(58) Field of Classification Search ................. 713/156; 705/51, 76, 1–3; 340/5.8–5.85
See application file for complete search history.

(56) References Cited

U.S. PATENT DOCUMENTS

| | | | |
|---|---|---|---|
| 5,224,163 A | 6/1993 | Gasser et al. | |
| 5,235,642 A * | 8/1993 | Wobber et al. | 713/156 |
| 5,530,438 A * | 6/1996 | Bickham et al. | 340/5.8 |
| 5,615,110 A * | 3/1997 | Wong | 705/38 |
| 5,659,616 A | 8/1997 | Sudia | |
| 5,712,914 A * | 1/1998 | Aucsmith et al. | 380/30 |
| 5,845,070 A * | 12/1998 | Ikudome | 726/28 |
| 5,878,138 A | 3/1999 | Yacobi | |
| 5,943,423 A * | 8/1999 | Muftic | 705/67 |
| 5,963,915 A * | 10/1999 | Kirsch | 705/26 |
| 5,983,208 A | 11/1999 | Haller et al. | |
| 5,995,756 A * | 11/1999 | Herrmann | 717/178 |
| 6,021,202 A * | 2/2000 | Anderson et al. | 705/54 |
| 6,047,270 A * | 4/2000 | Joao et al. | 705/44 |
| 6,064,990 A | 5/2000 | Goldsmith | |
| 6,105,010 A | 8/2000 | Musgrave | |
| 6,111,506 A | 8/2000 | Yap et al. | |
| 6,119,230 A * | 9/2000 | Carter | 726/5 |
| 6,157,953 A | 12/2000 | Chang et al. | |
| 6,275,941 B1 * | 8/2001 | Saito et al. | 713/201 |
| 6,311,163 B1 * | 10/2001 | Sheehan et al. | 705/2 |
| 6,321,339 B1 * | 11/2001 | French et al. | 713/201 |
| 6,353,886 B1 * | 3/2002 | Howard et al. | 713/156 |
| 6,408,330 B1 * | 6/2002 | DeLaHuerga | 709/217 |
| 6,418,467 B1 | 7/2002 | Schweitzer et al. | |
| 6,424,249 B1 * | 7/2002 | Houvener | 340/5.82 |
| 6,442,526 B1 | 8/2002 | Vance et al. | |

(Continued)

FOREIGN PATENT DOCUMENTS

EP 0 786 728 7/1997

(Continued)

OTHER PUBLICATIONS

Menezes et al. "Handbook of Applied Cryptography", 1997, CRC Press LLC, pp. 559-566.*

(Continued)

*Primary Examiner*—Ayaz Sheikh
*Assistant Examiner*—Matthew T Henning
(74) *Attorney, Agent, or Firm*—Fish & Richardson P.C.

(57) ABSTRACT

A managed authentication service provides relying parties an out-sourced authentication service for verifying the identity of online visitors. The service provides real-time, managed authentication and usage monitoring, multiple identity confirmation levels and a highly scalable and secure solution for authenticating online transactions.

23 Claims, 4 Drawing Sheets

U.S. PATENT DOCUMENTS

| | | | |
|---|---|---|---|
| 6,601,192 B1 | 7/2003 | Bowman-Amuah | |
| 6,931,545 B1* | 8/2005 | Ta et al. | 713/156 |
| 6,934,838 B1* | 8/2005 | Boyce et al. | 713/156 |
| 6,965,881 B1 | 11/2005 | Brickell et al. | |
| 7,062,471 B1* | 6/2006 | Matsuyama et al. | 705/65 |
| 7,106,843 B1* | 9/2006 | Gainsboro et al. | 379/191 |
| 7,295,988 B1* | 11/2007 | Reeves | 705/3 |
| 2001/0037388 A1* | 11/2001 | Suzuki | 709/225 |
| 2002/0083014 A1 | 6/2002 | Brickell et al. | |
| 2002/0120573 A1* | 8/2002 | McCormick | 705/50 |
| 2003/0086594 A1* | 5/2003 | Gross | 382/118 |
| 2005/0198356 A1 | 9/2005 | Delaney et al. | |
| 2005/0198536 A1 | 9/2005 | Brickell et al. | |

FOREIGN PATENT DOCUMENTS

| | | |
|---|---|---|
| EP | 0 848 338 | 6/1998 |
| JP | 2001-134534 | 5/2001 |
| JP | 2002-222251 | 8/2002 |

OTHER PUBLICATIONS

AberdeenGroup "Evaluating the Cost of Ownership for Digital Certificate Projects", 1998, Aberdeen Group Inc. "www.directoryservice.com/WP/Aberdeen/EvalCOO.htm".*

Matonis, "User-Friendly Digital Signatures", Oct. 2000, Hush Communications, "www.consult.hyperion.co.uk/PDFlibrary/y2000/matonis.pdf".*

Magic, Inc. "Meteor Security: Some Speculations", Aug. 2000, Magic Inc. "www.immagic.com/TOC/elibrary/TOC/meteor/downloads/MeteorSecurity.pdf".*

State of Colorado Senate Bill 97134 LLS No. 970530.01, www.state.co.us/gov_dir/leg_dir/sbills/SB134.htm, 1991.*

"E-Transactions Just Got a Loft Safer," http://www.valicert.com, 3 pp.

An Infrastructure for Authentication, Authorization and Delegation, Harold Myrvang, May 22, 2000, 100 pages.

Simple Public Key Certificate, C. Ellison, et al., Jul. 26, 1999, pp. 1-44.

SPKI Certificate Theory, C. Ellison, et al., Sep. 1999, pp. 1-41.

SPKI Examples, C. Ellison, et al., Mar. 10, 1998, pp. 1-15.

SPKI Requirements, C. Ellison, Sep. 1999, pp. 1-14.

* cited by examiner

MANAGED AUTHENTICATION SERVICE

BACKGROUND

Cryptography provides the basis for a number of privacy and authentication mechanisms used in computer-based systems. One such mechanism is a digital signature, which is often used to authenticate the sender of an electronic message. To create a digital signature, the sender first creates a private signature key and a corresponding public verification key. To sign a message or other document, the sender performs a computation that takes as input the message and the private signature key and produces as output a digital signature for that message. To verify a digital signature, a receiver performs a computation that takes as input the message, the digital signature for that message, and the public verification key, and produces as output either "signature verified" or "signature failed to verify."

In order to facilitate the authentication of a digitally signed document, the receiver must be assured that the public verification key that is used to verify the signature is indeed the public verification key belonging to the sender of the message. Typically, the receiver will obtain a digital certificate, which contains the identity of the sender, the public verification key of the sender, and other information. Typically, this digital certificate is digitally signed by a certification authority. Other mechanisms are also used for establishing the correspondence between an identity and a public verification key such as an entry in a database.

DESCRIPTION

A user's "digital credential", as used herein, refers to the security mechanisms associated with the user's identity. A user might have a variety of available security mechanisms. For example, a user's digital credential can include one or more digital signature keys relating to one or more digital certificates. In addition, a user may authenticate himself using one or more biometrics, a signature key from a smart card, a signature key from software or a signature key stored on a remote server and downloaded as needed. The user may invoke one or more of these mechanisms, depending on the situation and which mechanisms are readily available.

Validating a user's digital credential, therefore, can include one or more tasks. Examples include verifying that the user's digital signature is valid using the public key in the user's digital certificate and validating the digital certificate, which can include several additional tasks such as using a key of the certification authority to validate that the digital signature on the digital certificate is valid, verifying that the digital certificate has not been revoked or suspended, and validating the key of the certification authority.

Figure 1:
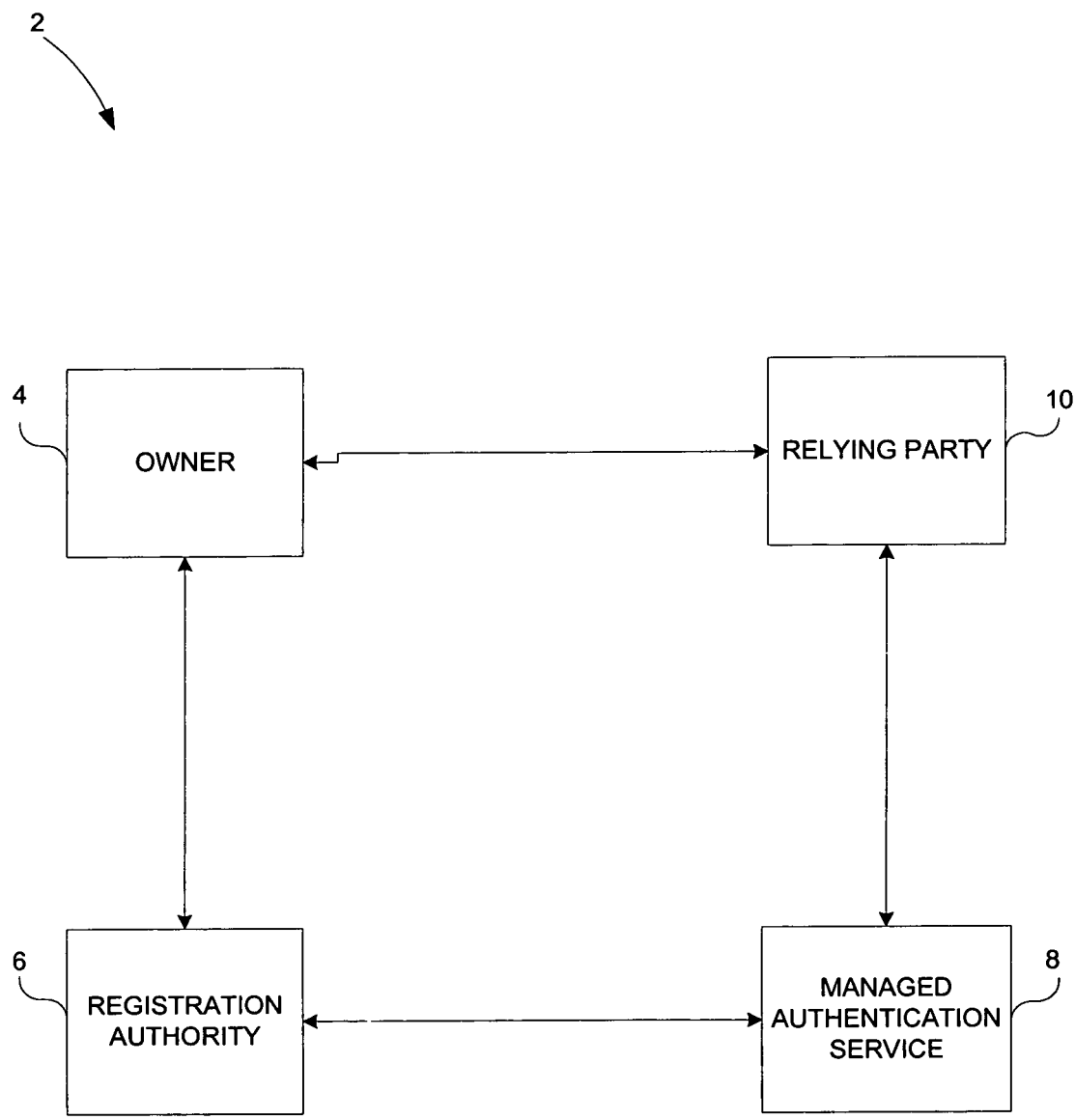
FIG. 1 is a block diagram illustrating one example of a system that manages digital credentials.

FIG. 1 is a block diagram illustrating one example of a system 2 that manages the use of digital credentials. More specifically, managed authentication service (MAS) 8 provides relying party 10 an out-sourced authentication service for verifying the identity of online visitors such as credential owner 4. As discussed in detail below, MAS 8 provides relying party 10 and owner 4 with real-time, managed authentication, usage monitoring, multiple identity confirmation levels and a highly scalable and secure solution for authenticating online transactions. Relying party 10 can determine whether the authentication mechanisms used by owner 4 is sufficient for the access being requested.

Relying party 10 represents any web-based provider of online goods or services. For example, relying party 10 can be a web-based retailer of consumer products such as books, software toys, games and the like. Alternatively, relying party 10 can be a business to business website such as an online marketplace for medical or other supplies. Other examples include online banking institutions, brokerage firms, and health care services. MAS 8 allows relying party 10 to focus on providing its online service knowing that the authentication process is remotely handled by MAS 8 and is based on leading technologies and consistent with government regulations. As such, relying party 10 is a customer of MAS 8 and accepts digital credentials managed by MAS 8.

Owner 4 can be any user that wishes to use a digital credential; however, owner 4 typically has an affiliation with the registration authority 6. For example, owner 4 may be a physician and registration authority 6 may be the American Medical Association (AMA) responsible for governing the registration of the physicians. In this example, MAS 8 is an out-sourced authentication service for healthcare service providers that want to offer higher levels of protection for confidential healthcare information. Registration authority 6 maintains "identity assets" for specific sets of professionals or consumers. MAS 8 collaborates with registration authority 6 such that relying party 10 can be sure that owner 4 is still a registered professional.

Registration authority 6 acts as an issuer of a digital credential for owner 4. Examples include the AMA and the American Pharmaceutical Association (APA). Registration authority 6 establishes policies, practices and procedures for enrolling owner 4. MAS 8 manages the distribution of the digital credentials and monitors their use, thereby insulating relying party 10 from the complexity of online authentication technology and enabling a higher level of online privacy and confidentiality. For example, MAS 8 provides real-time authentication and usage monitoring.

When a digital credential is used, MAS authenticates the owner in real-time and the transaction is reported in an activity log, which is available to the owner 4, registration authority 6 and relying party 10. MAS 8 monitors the usage of the digital credentials in order to detect misuse. Real-time authentication enables the digital credential to include more information than a conventional digital certificate. It also enables dynamic information to be used in the authentication process. The digital credential can, therefore, be updated in real-time to reflect changes in the owner's registration status, so relying party 10 can allow or deny access based on the most current user information available.

The digital credential issued by registration authority 6 is a collection of authentication mechanisms coupled with dynamic data. Its two-part design enables both the verification of a previously established identity and the real-time confirmation that the identity is still valid. Registration authority 6 creates and issues digital credentials in real-time, except where the enrollment process specifically demands off-line confirmation to establish a higher level of identity confirmation. Real-time enrollment is an important advantage in on-line transactions. For example, a physician who visits a relying parties' web site, but does not have a digital credential issued by the AMA, can be redirected to the enrollment page of registration authority 6. Upon successful enrollment, the physician can be redirected back to relying party 10.

When owner 4 receives a digital credential from registration authority 6, the digital credential is stored on his or her computer and corresponding information is stored by MAS 8. Multiple owners can store private digital credentials on the same computer. When the owner accesses relying party 10, the appropriate digital credential is automatically selected for use.

Owner 4 uses the digital credential to securely access relying part 10, present digitally signed documents and otherwise conduct secure transactions. In one configuration, owner 4 uses a conventional web browser to establish a secure communication link with a web server using a secure communications protocol, such as the Secure Socket Layer (SSL). When accessed, the web server issues a "challenge" to the web browser, which responds by signing the challenge with the private signature key and communicating the digital credential and the signed challenge to relying party 10. In another configuration, owner 4 uses his private signature key to digitally sign a document presented to relying party 10, such as when owner 4 is submitting a confidential medical diagnosis or a prescription request to a web-based health care service.

As described in detail below, the verification process involves a signed challenge-response that is typical in public-private key infrastructure (PKI) authentication. MAS 8 dynamically maintains the credential information, enabling a real-time verification that removes many of the latencies often associated with data updates. More specifically, MAS 8 checks the owner's identity validation information to ensure that no misuse has been reported and also confirms that the owner holds a valid registration with registration authority 6. The information maintained by MAS 8 is updated daily from registration authority 6. This offers relying party 10 a high degree of assurance that they are interacting with a valid registered owner.

Some on-line applications and services require different levels of identity confirmation based on the sensitivity of the information being accessed. Therefore, in one configuration every digital credential stipulates an identity confirmation level. Policies for assigning the confirmation levels are determined by registration authority 6. During the authentication process, MAS 8 passes the confirmation level to relying party 10 so it can be used to control access to sensitive information.

For example, five possible levels of identity confirmation for physicians include a student level, a professional level, a confirmed level, a notarized level and an agent level. The student level is for medical students who are attending an accredited U.S. medical school. The professional level is available for all physicians. Physicians input their name, state, zip code, date of birth, social security number and medical license number. This information is matched against information maintained by registration authority 6. The confirmed level is an upgrade from a professional level when owner 4 accesses authentication authority 6 and correctly enters a confirmation code, which may be communicated to owner 4 via the phone or through the postal service. The digital credential is upgraded from the professional level to the confirmed level upon confirmation of the information. The notarized level is the next level and indicates that registration authority 6 has a form on file that is signed by the physician and notarized by a licensed notary public. The local registration agent level is the highest level and indicates that a local registration agent enrolled the physician in person.

MAS 8 manages all authentication events and transactions, records those events, and makes the information available as appropriate to relying party 10, registration authority 6 and owner 4. This auditing capability provides the foundation for enhanced fraud detection. Relying party 10 can view a history of authentication activities that have occurred on its web site. For each activity, relying party 10 can view the owner name, the time of authentication, the confirmation level for the corresponding digital credential, the success or failure of the authentication and any parameters that were confirmed at the time of authentication.

Similarly, owner 4 can view information for his or her digital credential including the issue date, the expiration date, the user supplied computer name and the unique ID. Owner 4 can view his or her activity log over a specified time period. Furthermore, owner 4 can readily change the private password protecting the digital credential. Owner 4 can revoke the digital credential at any time and can terminate his or her digital credential.

Relying party 10 can integrate the load authentication service provided by MAS 8 at any point in its web site and can create its own access control policies to meet its needs for privacy and confidentiality. Furthermore, relying party 10 can customize the authentication interface such that it matches the look and feel of its web site. Therefore, if desired, the role of MAS 8 in the authentication process can be completely transparent to owner 4.

MAS 8 provides all systems for generating, validating and monitoring digital credentials. Furthermore, MAS 8 facilities are equipped with multiple security systems including system management software and the activity logs that contain a record of all authentication activities, as discussed below. Furthermore, the MAS 8 facilities are designed and built to safeguard critical information using multiple levels of overlapping security. Physical access is restricted to operational personnel only, it is monitored by camera in control via guards and magnetic card locks. Multiple checkpoints are used throughout each facility to further restrict access to sensitive information. Access to systems and information is carefully controlled through a high level of network and functional security at the perimeter of the secured facility, within the facility itself and in the connections to the client's systems.

Figure 2:
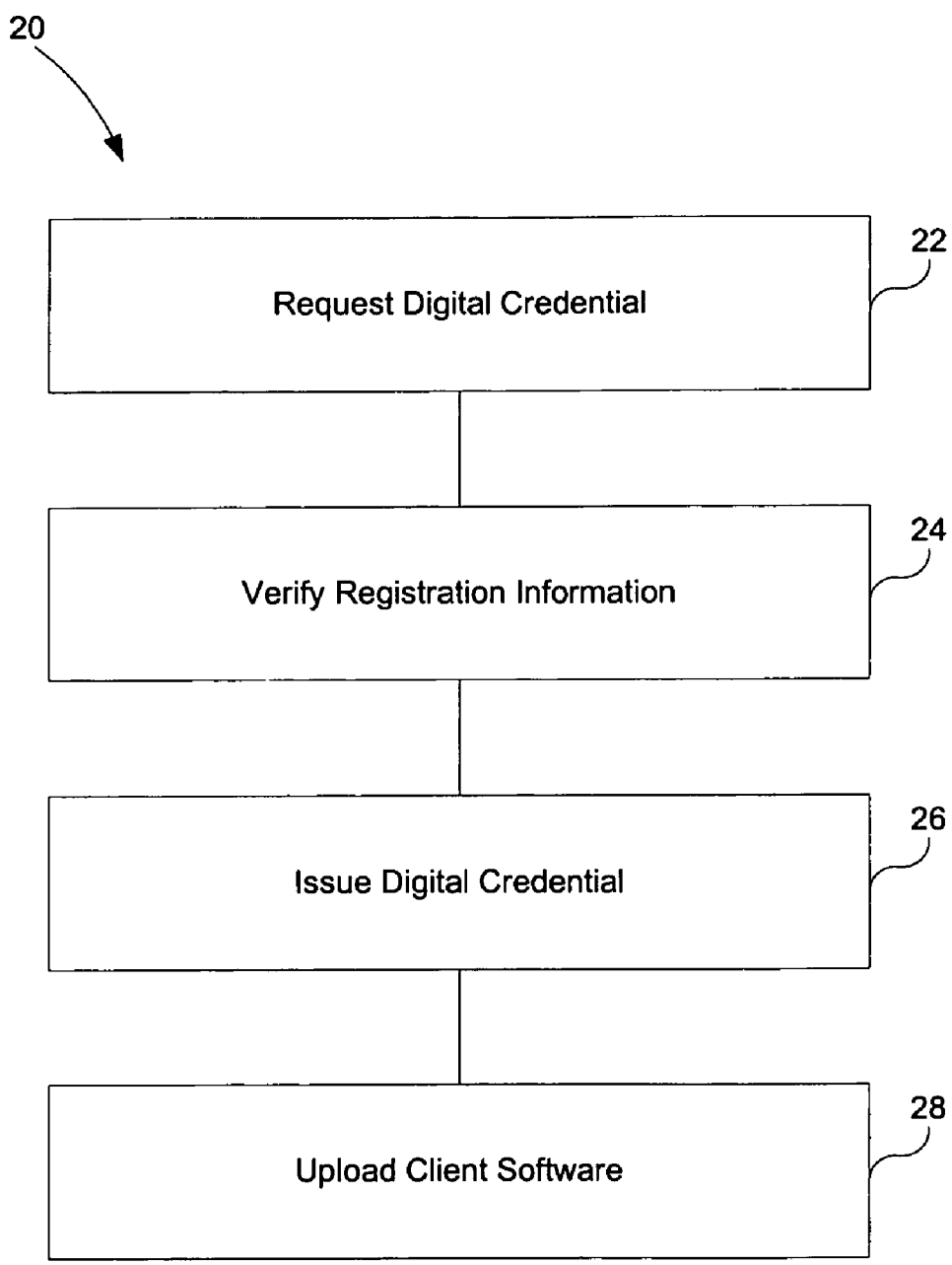
FIG. 2 is a flow chart illustrating one example of a process for issuing a digital credential.

FIG. 2 is a flowchart illustrating how an owner 4 obtains a digital credential from registration authority 6. In this example, it is assumed that owner 4 does not already have a digital credential or an account with relying party 10, and that he begins by accessing registration authority 6 directly. However, owner 4 could just as easily have accessed relying party 10 and have been redirected to registration authority 6. First, owner 4 contacts the web site of registration authority 6 using a standard Internet browser and requests a digital credential (22). Upon receiving this request, registration authority 6 asks for identifying information consisted with registration information maintained by registration authority 6. For example, registration authority 6 may ask for information relating to a physician's medical practice and license number. Registration authority 6 compares the submitted information to the information on file in order to verify the submitted information (24). Upon verifying the information, registration authority 6 issues a digital credential having the selected user identifier and confirmation level (26). At this point, client software is uploaded to the computer of owner 4 (28). As described below this client software enforces real-time authentication of the digital credential.

Figure 3:
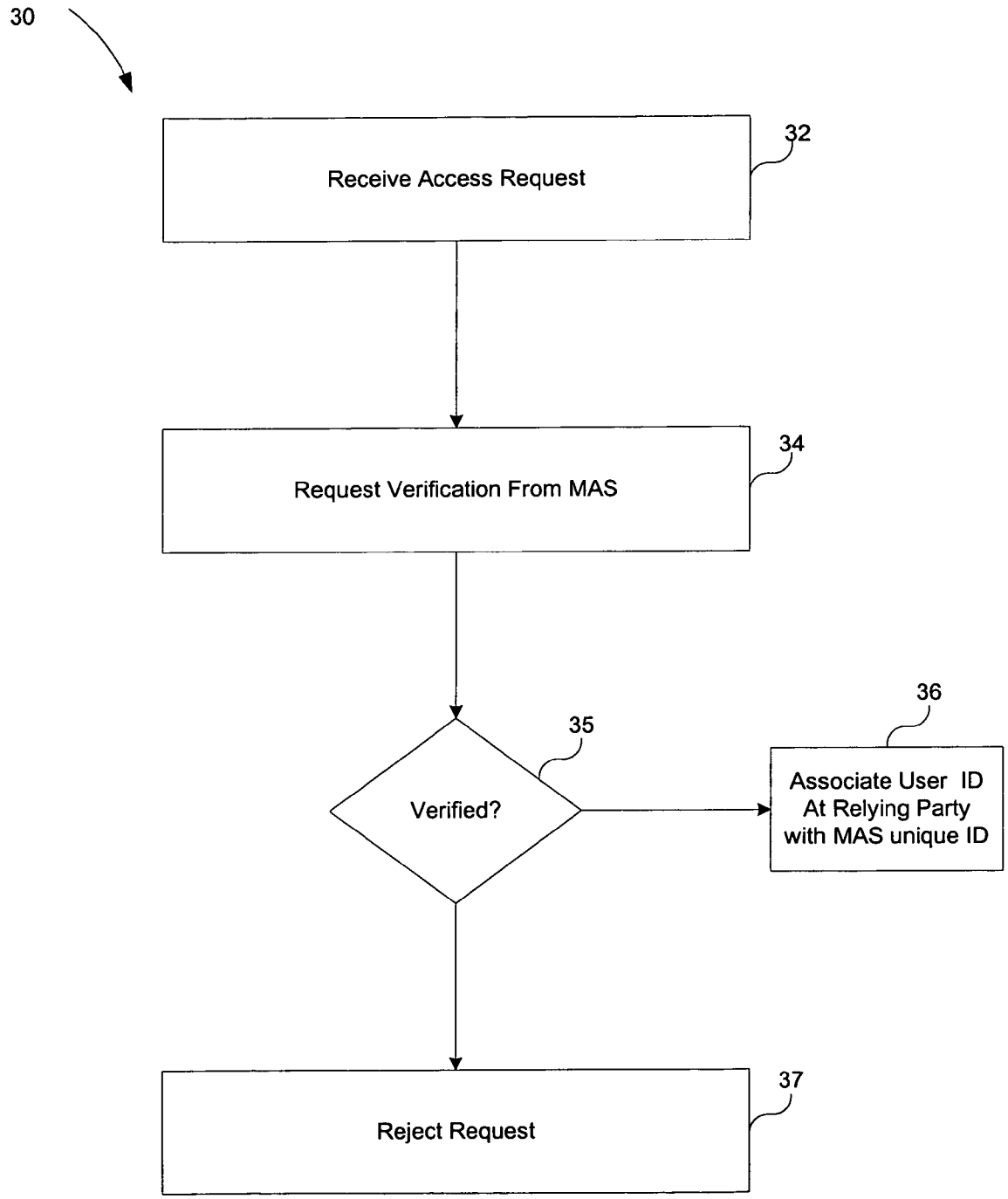
FIG. 3 is a flowchart illustrating an example process by which a relying party authenticates and registers an owner of a digital credential.

FIG. 3 is a flowchart illustrating an example process 30 of how an owner 4 is authenticated when he or she accesses relying party 10. After the owner 4 has received the digital credential, he or she typically accesses relying party 10 in order to take advantage of an on-line service (32). Upon receiving an access request, relying party 10 asks owner 4 for his or her user ID in order to initiate the authentication process. Upon receiving the ID, relying party 10 may communicate the ID to MAS 8 and requests that MAS 8 verify the identity of owner 4 (34).

At this point owner 4 is asked to enter his or her private password if it is needed to unlock the digital credential. MAS 8 performs the necessary cryptographic operations to validate that owner 4 is registered with registration authority 6 in good standing (35). Generally, MAS 8 performs various cryptographic measures in combination with verifying the registration information maintained by registration authority 6 in order to validate a digital credential of owner 4.

For example, MAS 8 may receive the digital credential, such as a digitally signed challenge and the digital certificate, from relying party 10 and uses the public key of registration authority 6 to verify the digital signature. Next, MAS 8 determines whether the owner 4 or another authorized party has revoked the digital credential. Finally, MAS 8 examines the registration information maintained by registration authority 6 to verify that the owner 4 is still a registered individual in good standing. Verification of good standing may include verification that no sanctions or other disciplinary action have been taken against owner 4 during a relevant period of time. In one configuration, MAS 8 stores a copy of the registration information maintained by registration authority 6. In this configuration the information is updated periodically, such as daily.

If the authentication fails, MAS 8 reports the failure to relying party 10, which rejects the access request from owner 4 (37). If the validation is successful, MAS 8 reports confirmation to relying party 10 and sends them a unique identifier to be associated with the user ID supplied by owner 4. In this manner, relying party 10 and MAS 8 can use the same unique identifier for owner 4 (36). On subsequent visits to relying party 10 by owner 4, the owner enters his or her user name which relying party 10 translates into the associated unique ID. At this point, relying party 10, transmits the unique ID to MAS 8 for authentication.

MAS 8 stores the result of the verification, whether successful or not, in activity log 20. In addition, MAS 8 stores relevant transaction information such as a date and time of the transaction, the relying party 10 that is involved in the transaction, the type of transaction, the device used to access relying party 10, such as a laptop computer, cell phone or a PDA, the value of the transaction, and location and position information, such as an IP address or a name of computing device 4.

Figure 4:
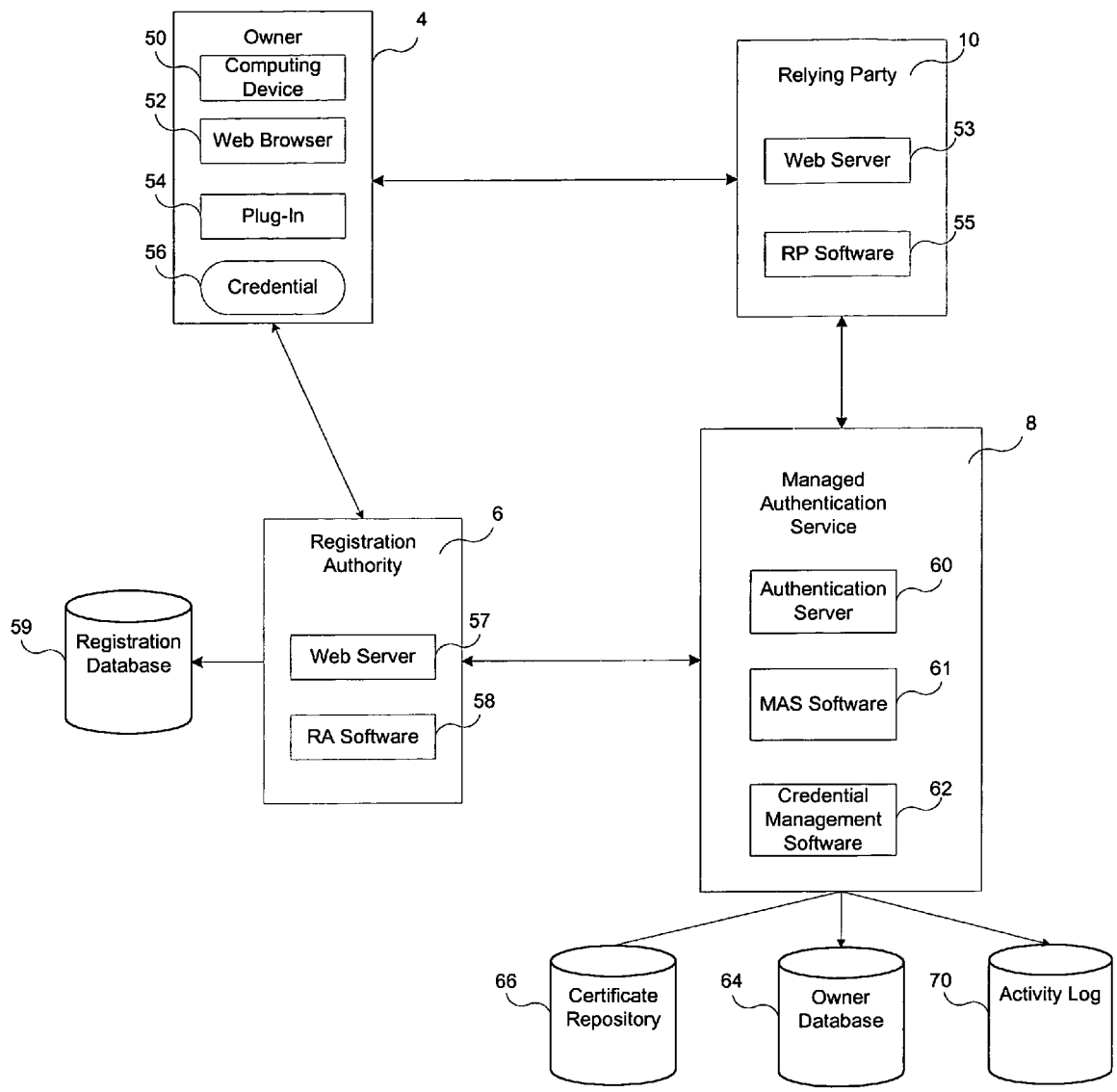
FIG. 4 is a block diagram illustrating an example of the managed authentication service in further detail.

FIG. 4 is a block diagram demonstrating system 2 in further detail. Owner 4 can use any general purpose computing device 50 suitable for interacting with a communication network, such as a packet-based digital network like the Internet. One example of a suitable computing device 50 is a personal computer. In addition, each computing device 50 can be a laptop computer, a handheld computer, a personal digital assistant (PDA), such as a Palm™ organizer from Palm Inc. of Santa Clara, Calif., or even a network-enabled cellular telephone.

In order to obtain digital credential, owner 4 directs web browser 52 to registration authority 6, generates a private signature key and a public verification key, and requests a digital certificate. Owner 4 then submits the public verification key and a variety of registration information, such as name, address and registration number, which registration authority 6 validates according to registration database 59 during the application process.

Plug-in 54 is designed to make the authentication process simple and intuitive for owner 4. In one configuration the plug-in is a JAVA applet and it is downloaded like any standard browser plug-in. Plug-in 54 resides on the owner's computer until deleted and supports the processes required for owner 4 to obtain, use and manage a digital credential issued by registration authority 6. This includes managing the secure processing of user passwords, the management of cryptographic keys, and the communication between plug-in 54 and relying party (RP) software 55.

Plug-in 54 connects and communicates with the web server 53 of relying party 10 or web server 57 of registration authority 6. It does not connect directly with MAS 8. Furthermore, multiple owners 4 can each use and manage their digital credentials on the same computer using a single plug-in 54.

For each digital signature presented by owner 4, plug-in 54 initiates a challenge-response sequence causing MAS 8, or alternatively relying party 10, to issue a challenge to owner 4. This assures that the digital signature is being produced in real-time and protects owner 4 from situations where someone acquires the digital credential temporarily and uses it to sign documents and impersonate owner 4 at a later time. Furthermore, the challenge can also include information that identifies relying party 10, so that the owner 4 can be assured that the message that he or she is signing can only be relied upon by that specific relying party. For example, the information may include a universal resource locator (URL) for relying party 10.

To participate in the managed authentication service provided by MAS 8, relying party 10 installs RP software 55 on web server 57 and integrates the software into their web site. In one configuration RP software 55 is JAVA-based such that it can be easily integrated into most computing environments.

Registration authority 6 maintains registration database 59 that stores "identity assets" for registered individuals, such as information relating to a physician's medical practice and license number. When owner 4 successfully applies for a digital credential 56, registration authority 6 submits the information to credential management software 62 of MAS 8 that, as a certificate authority, issues a corresponding digital credential 56, including a digital certificate and signature key, and records the owner information in owner database 64. In this fashion, the user becomes the "owner" of his or her digital credential 56.

When verifying the identity of owner 4 in real-time, MAS 8 confirms that owner 4 is still a licensed with registration authority 4 in good standing. In one configuration, MAS software 61 executing on MAS server 60 checks owner database 64, which contains a copy of the information maintained by registration authority 6. Credential management software 62 periodically contacts registration authority 6 to update owner database 64 to ensure that owner database 64 has up-to-date registration information. In another configuration, MAS 8 accesses registration authority 4 for each verification request.

Because MAS 8 not only employs cryptographic techniques to verify the identity of owner 4 but provides real-time confirmation that he or she is a registered individual in good-standing with registration authority 6, MAS 8 may charge relying party 10 on a per-verification basis. Other billing models exist including charging relying party 10 a subscription fee to its managed authentication service, bulk usage, limited prepaid usage (debit), and per user billing. MAS 8 and relying party 10 may for a legal contract dictating the terms of the service.

In order to further increase security, MAS 8 may require that relying party 10 sign its portions of any secure transaction. For example, MAS 8 may require that an online pharmacy (relying party 10) sign a prescription form before communicating the form to a pharmacist for completion. The pharmacist (owner 4) signs it after the form has been signed by the online pharmacy. This helps mitigate against certain attacks because a website would be prevented from sending fraudulent forms to a registered user for signing and then present them to the online pharmacy. By having each party sign their portion of these transactions, and by having MAS involved in each transaction, MAS 8 is able to identify actions or failures to act and thereby assign associated liabilities and provide irrefutable proof mechanisms supporting such assignments. This can limit the potential liabilities of each party and provide a foundation so each party can provide assurance that they correctly performed their task.

In addition, MAS 8 incorporates many features that allow an owner or delegate to detect unauthorized use of the digital signature key in the event digital signature key is misappropriated or otherwise misused. For example, when verifying digital signature during each secure transaction, MAS software 61 can automatically send an activity report to web browser 52, which can display the activity report to the owner. In this fashion the user can readily identify whether the digital signature key is being misused.

Owner 4 can access registration authority 6 and request an activity report that details any usage of digital signature key. Upon receiving such a request, registration authority 6 communicates the request directly to MAS 8. In response, MAS 8 examines activity log 70, extracts the relevant activity information, formulates a report and communicates the report to registration authority 6, which electronically presents the report to owner 4. The owner can also configure registration authority 6 to periodically generate the report and electronically mail the report to the user. Alternatively, registration authority 6 can mail a physical copy of the report to the user.

The invention has been described in reference to a variety of embodiments. These and other embodiments are within the scope of the following claims.

What is claimed is:

1. A machine-implemented method comprising:
   receiving digital credential information from a relying party at an authentication service, wherein the digital credential information is indicative of a first user being professionally licensed but has been received by the relying party from an unauthorized user;
   verifying that the digital credential information is valid using professional license status information that has been stored for a plurality of users;
   providing verification information indicative of a valid professional license of the first user from the authentication service to the relying party; and
   providing information from the authentication service to the first user, the information indicative of the provision of verification information indicative of the valid professional license to the relying party,
   wherein the relying party, the unauthorized user, and the first user are distinct from each other.

2. The method of claim 1, wherein providing information to the first user comprises providing access to an activity log associated with the first user.

3. The method of claim 1, wherein:
   the professional license status information comprises registration information indicative of a professional license registration status with a registration authority; and
   the method further comprises, prior to providing the verification information to the relying party, verifying the registration information with the registration authority.

4. The method of claim 1, wherein:
   the professional license status information comprises registration information indicative of a professional license registration status with a registration authority; and
   the method further comprises verifying the registration information with the registration authority.

5. The method of claim 1, further comprising:
   storing access information associated with the relying party, the access information including information indicative of the providing the verification information; and
   providing the access information to the relying party.

6. The method of claim 1, further comprising at least one of the relying party and the authentication service issuing a challenge in response to receiving digital credential information associated with the first user.

7. The method of claim 1, further comprising receiving, at the relying party, the valid digital credential information from an unauthorized user.

8. The method of claim 1, wherein verifying that the digital credential information is valid comprises verifying that no disciplinary action has been taken against the first user.

9. An article comprising a machine-readable medium embodying information indicative of instructions that when performed by one or more machines of an authentication service result in operations comprising:
   receiving digital credential information from a relying party at the authentication service, wherein the digital credential information is indicative of a first user being professionally licensed but has been received by the relying party from an unauthorized user;
   verifying that the digital credential information is valid using professional license status information that has been stored for a plurality of users;
   providing verification information indicative of a valid professional license of the first user from the authentication service to the relying party; and
   providing information from the authentication service to the first user, the information indicative of the provision of verification information indicative of the valid professional license to the relying party,
   wherein the relying party, the unauthorized user, and the first user are distinct from each other.

10. The article of claim 9, wherein providing information to the first user comprises providing access to an activity log associated with the first user.

11. The article of claim 9, wherein:
    the professional license status information comprises registration information indicative of a professional license registration status with a registration authority; and
    the operations further comprise, prior to providing the verification information to the relying party, verifying the registration information with the registration authority.

12. The article of claim 9, wherein:
    the professional license status information comprises registration information indicative of a professional license registration status with a registration authority; and
    the operations further comprise verifying the registration information with the registration authority.

13. The article of claim 9, wherein the operations further comprise:

storing access information associated with the relying party, the access information including information indicative of the providing of the verification information; and providing the access information to the relying party.

14. The article of claim 9, wherein verifying that the digital credential information is valid comprises verifying that no disciplinary action has been taken against the first user.

15. A system comprising: storage configured to store professional license status information for a plurality of users; and an authentication service configured to:
receive digital credential information from a relying party, wherein the digital credential information is indicative of a first user being professionally licensed;
verify the digital credential information using the professional license status information;
provide verification information indicative of a valid professional license of the first user to the relying party; and
provide information to the first user, the information indicative of the provision of verification information indicative of the valid professional license to the relying party,
wherein the authentication server is configured to provide the information indicative of receipt of valid digital credential information without regard to whether the relying party has received the valid digital credential information from the first user,
and wherein the relying party is distinct from the first user.

16. The system of claim 15, wherein the authentication service is configured to provide information to the first user at least by providing access to an activity log associated with the first user.

17. The system of claim 15, wherein the authentication information comprises registration information indicative of a registration status with a registration authority, and wherein the authentication service is further configured to:
verify the registration information with the registration authority prior to providing the verification information to the relying party.

18. The system of claim 15, wherein:
the professional license status information comprises registration information indicative of a professional license registration status with a registration authority; and
the authentication service is further configured to verify the registration information with the registration authority.

19. The system of claim 15, wherein the authentication service is further configured to:
store access information associated with the relying party, the access information including information indicative of the providing the verification information; and
provide the access information to the relying party.

20. The system of claim 15, wherein the authentication service is further configured to issue a challenge in response to receiving digital credential information associated with the first user.

21. The system of claim 15, wherein the authentication server is configured to provide the information in response to the relying party having received the valid digital credential information from an unauthorized user.

22. The system of claim 15, further comprising a relying party configured to receive the digital credential information associated with the first user and relay it to the authentication service.

23. The system of claim 15, wherein the authentication service configured to verify the digital credential information by verifying that no disciplinary action has been taken against the first user.

* * * * *